United States Patent [19]
Griset, Jr.

[11] 4,184,316
[45] Jan. 22, 1980

[54] PRODUCTION OF NOVELTY YARNS

[75] Inventor: Ernest J. Griset, Jr., Asheville, N.C.

[73] Assignee: Akzona Incorporated, Asheville, N.C.

[21] Appl. No.: 887,611

[22] Filed: Mar. 17, 1978

Related U.S. Application Data

[62] Division of Ser. No. 722,881, Sep. 13, 1976, Pat. No. 4,080,777.

[51] Int. Cl.$^2$ ............................................. D02G 3/34
[52] U.S. Cl. .................................... 57/295; 57/206; 57/241; 57/350; 28/252
[58] Field of Search ............... 57/34 B, 35, 149, 753, 57/140 C, 140 J, 164, 157 F, 206, 241, 258, 350, 295; 28/252, 271

[56] References Cited

U.S. PATENT DOCUMENTS

| | | | |
|---|---|---|---|
| 3,083,522 | 4/1963 | Rakowski et al. | 57/34 B |
| 3,105,349 | 10/1963 | Palm et al. | 57/34 B |
| 3,144,747 | 8/1964 | Palm et al. | 57/34 B |
| 3,269,105 | 8/1966 | Eldridge et al. | 57/140 J |
| 3,438,194 | 4/1969 | Cerutti et al. | 57/140 J X |
| 3,453,709 | 7/1969 | Dyer | 57/34 B X |
| 3,609,835 | 10/1971 | Boon | 28/252 X |
| 4,058,968 | 11/1977 | Benson | 57/157 F X |

*Primary Examiner*—Gorenstein Charles
*Attorney, Agent, or Firm*—Craig and Antonelli

[57] ABSTRACT

A novelty yarn having a pronounced variation in linear density is obtained by passing at least one multifilament yarn through a fluid tangling zone and by alternatingly and mechanically tensioning and relaxing the yarn within the tangling zone.

9 Claims, 7 Drawing Figures

PRODUCTION OF NOVELTY YARNS

This is a division of application Ser. No. 722,881, filed Sept. 13, 1976, now U.S. Pat. No. 4,080,777, issued Mar. 28, 1978.

This invention relates to novelty yarns having pronounced variations in linear density, especially beaded or slubbed yarns for producing shantung fabric and the like effect fabrics as well as dental floss and other effect yarns under a process and an apparatus for producing such yarns.

BACKGROUND OF THE INVENTION

The manufacture of novelty yarns from combined ends is old in the art. Examples of novelty yarn involve combining untextured ends with no overfeed, one end being overfed at a rate greater than the other end; combining a falsetwist textured "core" yarn with a "flat" effect yarn; combining falsetwist textured "core" and "effect" yarns; among others.

U.S. Pat. No. 3,264,816 discloses a synthetic yarn wrapped with a staple fiber which is then combined with a core yarn.

U.S. Pat. No. 3,756,005 discloses a process for producing a novelty effect yarn by passing two yarns through a falsetwisting device and overfeeding one yarn into the falsetwist device with the use of an aspirator-type jet. The slubs formed along the core yarn are somewhat random in nature.

U.S. Pat. No. 3,474,613 discloses a novelty product made using an aspirating jet and a "slubbing" jet in combination in which the aspirating jet forces one end of yarn onto a foraminous surface, afterwards from which the textured yarn is combined with another yarn in the slubbing jet. The yarns are thereafter passed respectively through a tangling jet and a falsetwist jet.

U.S. Pat. No. 3,691,750 discloses a continuous filament falsetwist textured core yarn wrapped with another falsetwist textured yarn of higher crimp amplitude, the wrapper filaments forming reversing helices at intervals along the length of the core yarn.

BRIEF DESCRIPTION OF THE PRESENT INVENTION

The present invention is directed to a process and apparatus for making distinct and pronounced variation in the linear density of a yarn. The process can also be used to produce multiple yarn composites of pronounced linear variation with one or more of the yarns capable of bearing stress along the length of the composite.

Further, the invention, as envisioned herein, can produce denier variations in multiple strand composites of different dyeabilities wherein denier variations will produce different slub effects along the length of the composite.

The method and apparatus herein may also be used to great effect to produce a dental floss yarn comprised of core yarn and effect yarn formed into beads and supported by a waxed or unwaxed yarn twisted with the core and effect yarns along the length of the composite.

The apparatus includes means for mechanically varying the tension of at least one strand of yarn while passing the yarn through a tangling jet. The intermittent fluctuation in tension of the yarn while passing through the jet produces alternating sections of compacted yarn and fluffed, nubby, loopy yarn.

Preferably, the tangling apparatus used is of the aspirating type so that yarn filaments are sucked into the jet apparatus when tensions are relaxed in the filaments. This sucking action permits one strand to be maintained in a tensioned state while passing through the jet simultaneously with a briefly nontensioned yarn strand whereby the action of the jet opens the filaments of the tensioned strand and intermingles therewith looped filaments of the tensionless strand. When the tensioned strand filaments close after passing through the jet device, the looped filaments are trapped, producing a fluffed effect so long as the effect strand remains untensioned. When both strands are tensioned, the filaments of each strand are intermingled, but the composite remains compact. Obviously, when three or more strands are fed through the jet device, the individual strands may be alternately relaxed to create numerous effects.

Preferably, there is provided some means of controlling the rate of passage of the various yarns through the tangling jet, such as positive drive nip rollers or tension devices. The maintenance of a positive feed with mechanical tension varying devices as disclosed herein permit accurate control of denier variations such as ratio of fluffed to compacted denier and distances and length of fluffed sections.

The invention is also concerned with a novelty yarn product having pronounced variations in linear density which comprises at least one multifilament yarn or strand having a plurality of alternating fluffed and compacted filaments arranged sequentially along its length. This yarn product may be further characterized by a significant bulk variance, i.e., the fluffed portions of the yarn have much greater bulk than the compacted or non-fluffed portions.

One embodiment of the novelty yarn is a composite product made up of at least one fluffed or beaded yarn and at least one support or core yarn combined along their lengths.

The process of this invention for producing novelty yarns comprises introducing at least one multifilament yarn or strand into a fluid tangling zone; alternatingly tensioning and relaxing the yarn within said tangling zone to form sequential and alternate portions or segments of compacted and fluffed filaments.

More particularly, this invention is directed to a process wherein a multifilament yarn is introduced into a fluid tangling jet and the path of the yarn to the jet is intermittently and abruptly changed, whereby the yarn is subjected to variations in tension during its travel to the tangling jet.

It will be understood that the feeder yarns used to produce the novelty yarns of this invention include synthetic and natural fibrillary materials such as nylons, polyesters, acrylic rayons, cellulose, and the like; especially suitable are textured polymeric yarns of nylon, polyester, and rayon.

This invention will be further understood from the following detailed description and the accompanying drawings wherein:

FIG. 1 schematically illustrates an apparatus and process for producing a two-composite beaded or slubbed novelty yarn;

Figure 1:
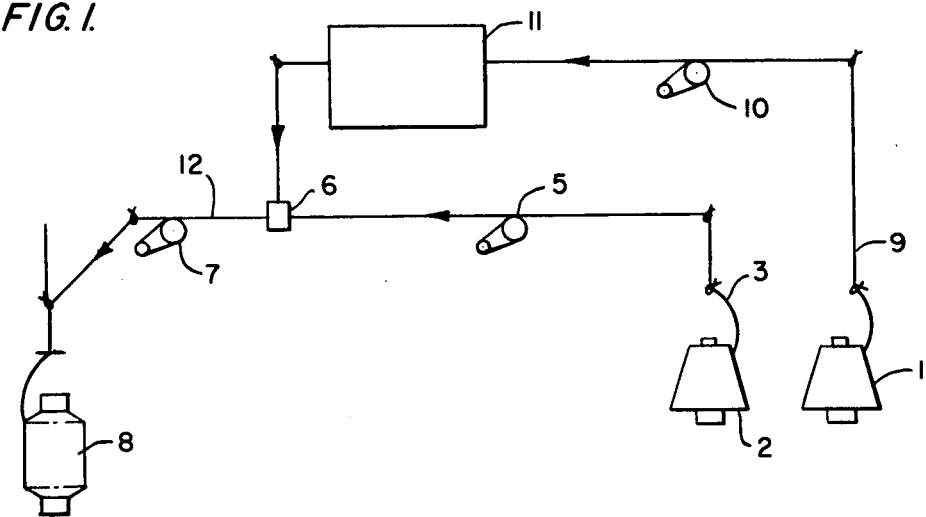

In FIG. 1, there is shown one embodiment of an apparatus for producing novelty yarn that comprises a core yarn and an effect yarn. A package 1 contains the effect yarn 9 and package 2 contains the core yarn 3. These yarns may be a polyester stretch textured yarn. Core yarn 3 is fed by the core roll 5 through the air tangling jet 6 and to the feed roll 7 and then the take-up package 8. The effect yarn 9 is fed by the effect roll 10 through a reciprocating device 11 and then into the air tangling jet 6 wherein the effect yarn 9 is combined with the core 3 yarn and follows the same path to the yarn take-up package 8. It will be understood that the combined yarn product 12 exiting from jet 6 is a beaded or slubbed yarn. The speed of the roll 5 and of roll 10 are the same and the yarn product 12 is overfed to the feed roll 7 by approximately 2-8%, and usually about 3.5%.

It will be appreciated that in the reciprocating device, the path of the effect yarn 9 is intermittently and abruptly changed by mechanical means so that the yarn is subjected to variations in tension during its travel to the tangling jet.

Generally, the effect yarn is positively displaced, i.e., shifted, from one travel path to another path within the reciprocating device. This displacement may be effected by a cam-operating arm, by a rotating pin or other like means, embodiments of which will be hereinafter described in greater detail.

Figure 2:
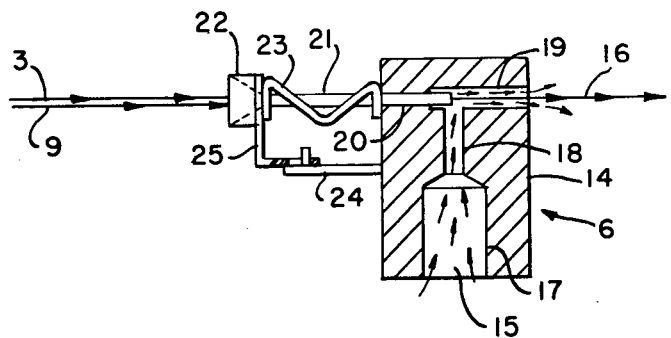
FIG. 2 shows a schematically elevated view of a fluid tangling jet for forming a beaded or slubbed yarn.

FIG. 2 schematically illustrates an embodiment of a pneumatically operated jet assembly that may be used as the gas tangling jet employed in the apparatus of FIG. 1. The jet assembly 6 includes a housing 14 having a gas inlet passage 5 and a gas outlet passage 16 arranged perpendicular thereto. Te gas inlet passage is formed by a large diameter bore 17 that tapers down to a small diameter bore 18.

The gas outlet passage is formed by a bore 19 that extends from one side of the housing to beyond the end of bore 18 and by a bore 20 of reduced diameter that extends through to the other side of the housing.

A hollow needle 21 is inserted into the housing in fluid-tight engagement within bore 20. The flow of gas by the needle creates a vacuum which sucks yarn through the orifice 22 at one end and out through the gas outlet passage when the discharge end of the needle is pushed beyond the gas orifice of the gas inlet passage.

After the yarn has been fed through the jet, the needle is released and is retracted by the action of spring 23. A bracket 24 is secured to housing 14 and provides an adjustable guide support for another bracket 25 secured to the orifice end of the hollow needle. These brackets serve to retain the hollow needle in proper position for normal operation as shown in FIG. 2.

It will be appreciated that the position of the discharge end of the hollow needle determines, in part, the character of the yarn product, i.e., the degree of variation of the denier of the novelty yarn product.

Figure 3:
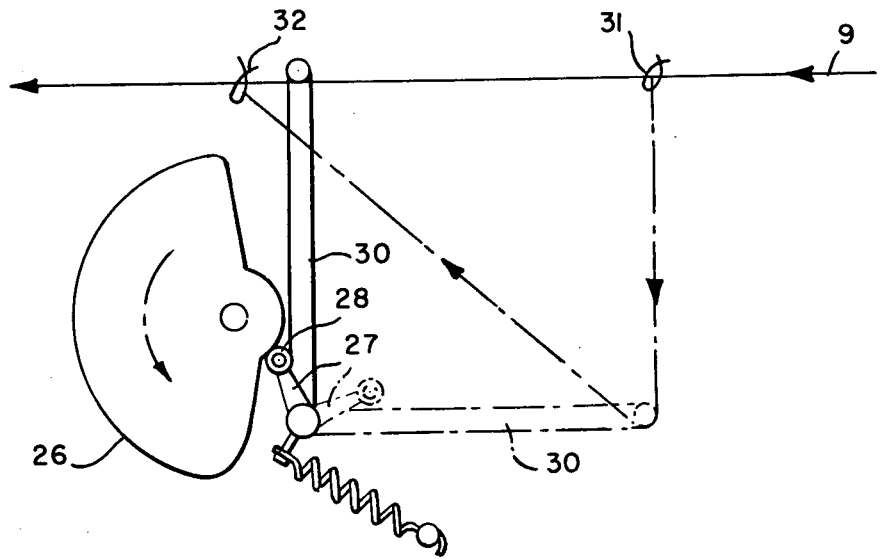
FIG. 3 is a schematic view of a reciprocating device or means for sequentially and alternatingly applying tension to a moving strand or yarn.

FIG. 3 shows an embodiment of the reciprocating device that may be employed in the apparatus of FIG. 1. This device has a cam element 26 rotating in a counter-clockwise direction as indicated by the arrow. Cam follower 27 with a nylon roller 28 is biased against the cam element and is mounted on a pivoted member 29. A yarn contracting arm 30 is operatively associated with follower 28. When the arm 30 is in the vertical position shown in solid lines, the yarn 9 passes through guides 31 and 32 without any effect and the cam element holds arm 30 in this position for several seconds, e.g., about 5 seconds, as the cam follower contacts the raised portion of the cam element, the arm 30 lowers the effect yarn from the normal position to the position shown in dashed lines thereby creating tension on the effect yarn. At the same time, the core yarn 3 is in a relaxed or tensionless state and is permitted to slightly overfeed into the jet increasing in size as it combines with the stretched portion of the effect yarn. The arm requires a short period of time, e.g., 1.5 to 2 seconds, to move from the vertical position to the horizontal position and remains in the horizontal position for several seconds, e.g., 5 seconds. During this period, no fluffing effect is given to the effect yarn. When the cam follower drops from the high point to the low point on the cam element, the effect yarn will rise quickly to a tensionless horizontal position. This abrupt rise or change in position will cause a sudden slack in the effect yarn so that a slub or fluff section will form in the yarn as the yarn enters the tangling jet to combine with the core yarn. The composite yarn product will also increase in diameter until the tensions in both yarns, i.e., the core yarn and the effect yarn, equalize again. This cycle of operation is repeated for each revolution of the cam element.

It will be appreciated that in the apparatus shown in FIG. 1 that the design of the cam element can be changed for different effects. Also, a pattern disturber, i.e., a device which holds the cam element in a position wherein no effect is created in the effect yarn, can be used to interrupt the rotation of the cam element, thereby changing the periodic character of the beads or slubs formed in the yarn.

Figure 4:
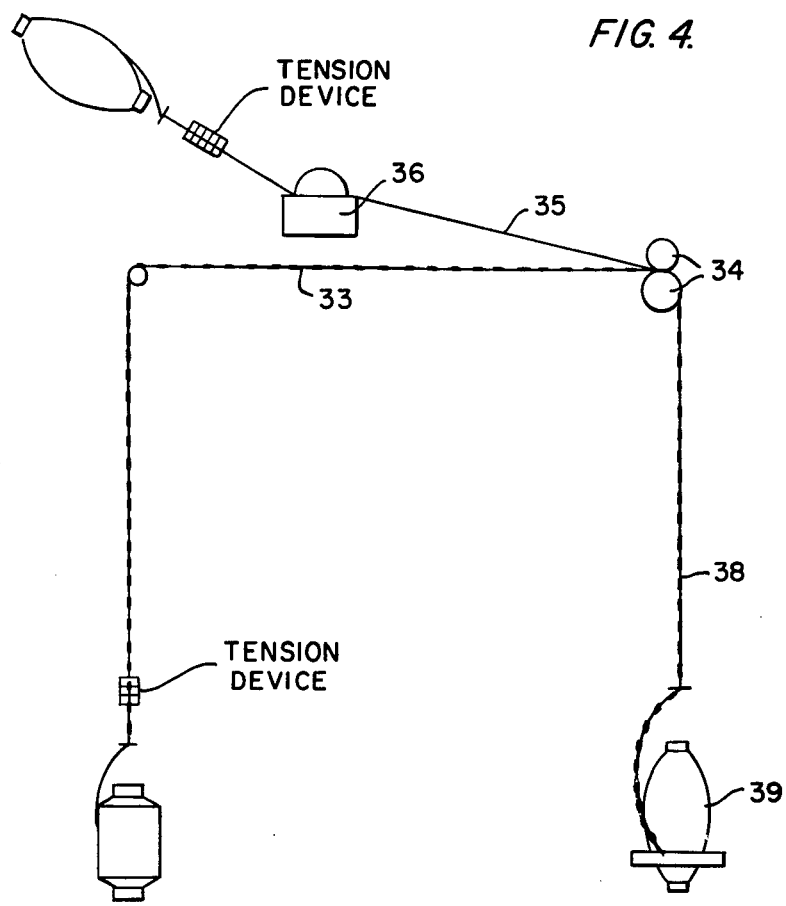
FIG. 4 shows a schematic arrangement and two-stage process for combining a waxed support yarn with a beaded yarn to form a dental floss.

One aspect of the present invention is directed to the production of a composite yarn product which is especially useful as a dental floss. The embodiment of the invention schematically shown in FIG. 4 is a two-stage process wherein a beaded nylon yarn which may be produced in the manner shown in FIG. 1 is combined with a waxed support yarn. Beaded composite yarn 33 is taken from a package and passed between the nip of a pair of combining rolls 34 wherein it is combined with a nylon support yarn 35 that has been passed through a wax applicator means 36. The composite nylon yarn 38 is taken up from the rolls and placed in a package 39. This package may be subsequently placed in a steam chest for a period of time sufficient to insure migration of the wax from the support yarn throughout yarn package, e.g., for about 2 hours in steam at 160° F. or lower.

Figure 5:
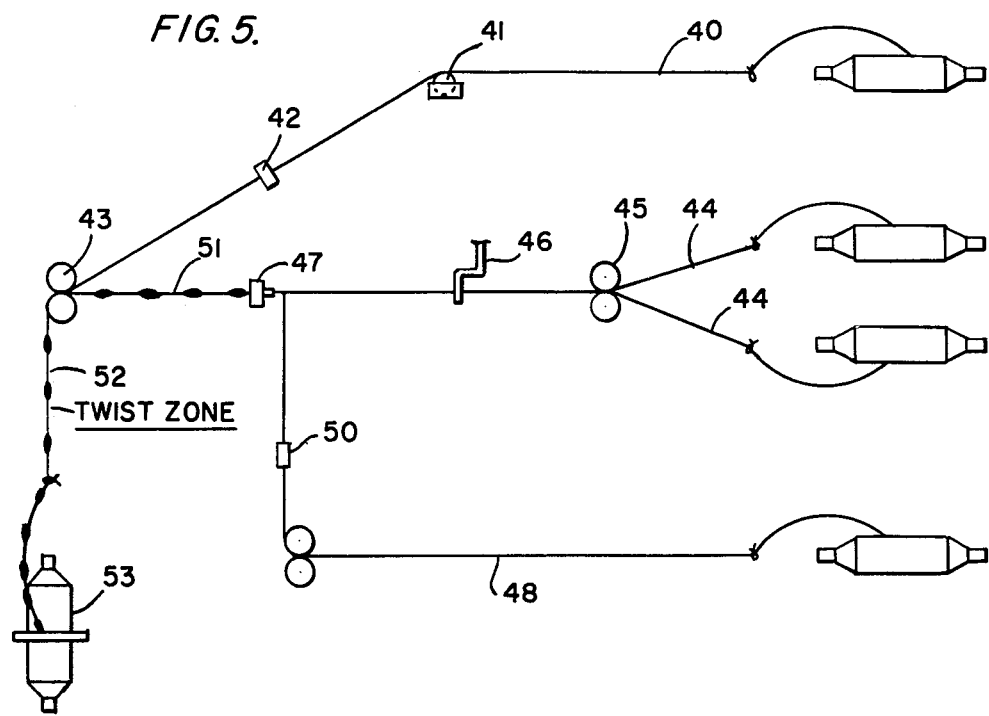
FIG. 5 illustrates a continuous one-stage process and apparatus for producing a dental floss from a support yarn, two effect yarns, and a core yarn.

Production of dental floss will be further understood from the following example wherein dental floss is produced in a one-stage continuous process as illustrated in FIG. 5.

A support yarn 40 (200/16 nylon 6) is passed through a wax applicator 41 wherein a roller applies 25% wax to the yarn. This yarn is then cooled by a fan cooling means 42 to solidify the wax and is passed to a pair of yarn combining rolls 43. Two effect yarns 44 of nylon 6, each having a denier of 200 and consisting of 64 filaments (200/64), were drawn through a pair of feed rollers 45 wherein the two yarns are combined. The resulting composite effect yarn is passed through reciprocating device 46 to an air tangling jet 47 wherein the effect yarn is combined with a core yarn 48 of nylon 6 (200/64). A pair of feed rollers 49 draws the core yarn from a package through a wet-out device 50 wherein water is added to the yarn. A beaded yarn composite 51 is taken from the jet and combined with the support yarn by rolls 43. The multistrand composite 52 exiting from these rolls is given a twist of 5.5 t.p.i. and taken up on the pirn 53.

Figure 6:
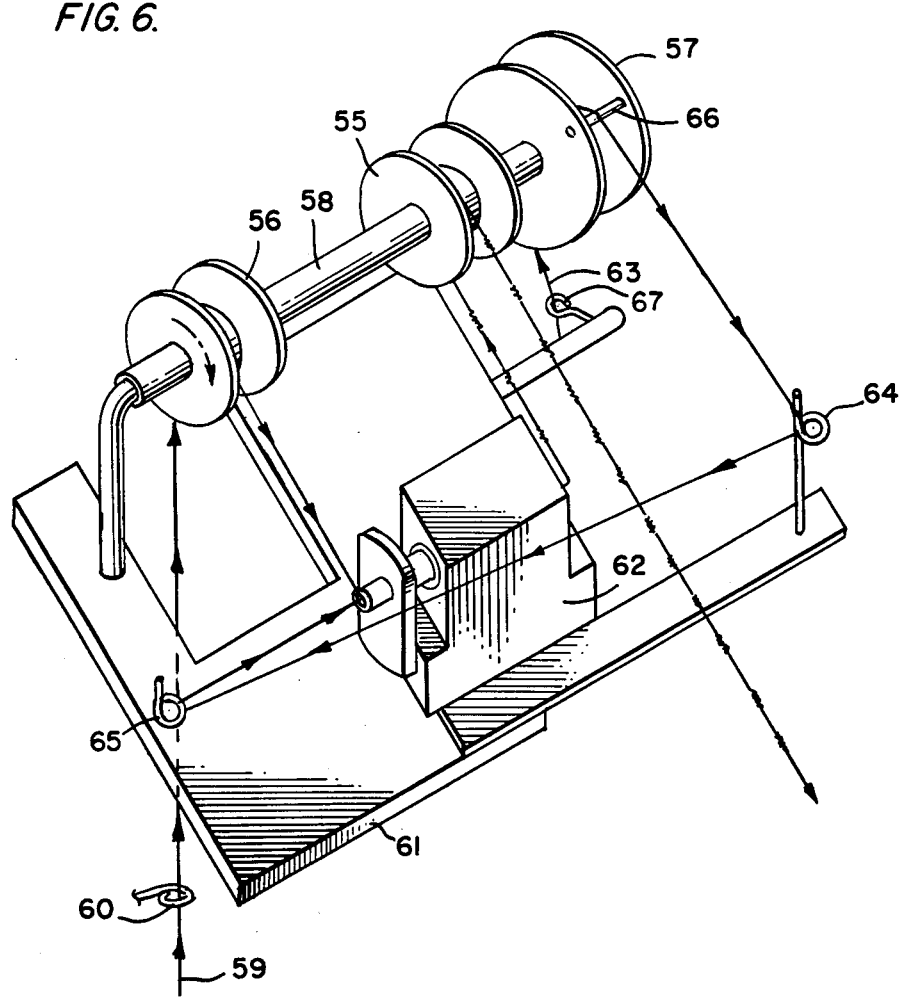
FIG. 6 shows a perspective schematic view of an apparatus for producing a beaded yarn in accordance with the arrangement shown in FIG. 5.

The characteristics of the beaded yarn, the support yarn and the resulting dental floss may be generalized as follows:

Beaded yarn:
Average denier—550-650
Distance between bends or fluffs—1¼″-1¾″
Length of fluff or bead—¾″-1¼″
Filaments—128
Yarn—Nylon 6
Support Yarn:
Denier—200
Filament—16
Fiber—nylon 6
Wax—25% (may be unwaxed if desired)
Dental Floss:
Ply twisted—4 to 8 t.p.i.
Total denier—700 to 900 (unwaxed); 750 to 1100 (waxed)
Filament—144
Breaking strength—3 to 5 pounds FIG. 6 illustrates one embodiment of an apparatus or device for producing a beaded yarn which uses a system of compound pulleys operatively associated with an air tangling jet. In this apparatus, the take off pulley 55 for the beaded yarn, the core pulley 56, and the effect producing pulley 57 are mounted on a single rotatable shaft 58. The core yarn 59 is guided via guide 60 which may be located below the support frame 61 from a pirn (not shown) to the core pulley 56 into he air tangling jet 62 (which is of the type illustrated in FIG. 2) and then is part of the beaded yarn passed to the take-off pulley 55 (which drives the shaft 58) and finally to a takeup package forming device. The effect yarn 63 comes from a spool below the frame 61 and is guided by a guide 67 mounted on a guide bar and then around the effect pulley to a guide 64 and guide 65 to enter into the jet where it combines with the core yarn.

The effect pulley has a pin 66 located on its outer periphery. The effect yarn is wrapped around the center shaft of the effect pulley (not shown) and the pin 66 to thereby cause alternating periods of tension and slack in the effect yarn. It will be recognized that this compound pulley arrangement has several advantages, i.e., the composite novelty yarn drives all three pulleys, the ratio of the size of one pulley to another, can be varied by replacing with a pulley of different diameter, the pulleys stop together when there is a break in the composite yarn product, and the degree of reciprocating movement provided by the effect pulley can be varied by changing the number of pins.

It will also be understood that the extent of bulk variance, as evidenced by the variation in linear density, in the beaded yarns will be also controlled by the amount of overfeed of the feeder yarns and that this is governed by the intended application. For example, in producing a beaded yarn for giving a shantung effect, the distance between beads or slubs may vary from 8 to 12 feet with a bead or fluff section or from ⅛ to 2″ long; whereas the beaded yarn for producing dental floss may have beads at a distance of from less than one inch to a few inches from each other with the bead length on the order of one end or more. Therefore, the overfeed for a beaded yarn to be used in shantung fabric may be up to about 5%, while the overfeed for a dental floss may be as much as 150%.

In producing the dental floss by use of the apparatus shown in FIG. 6, the overfeed of the core yarn is about 10% and that of the effect yarn is 150%.

Figure 7:
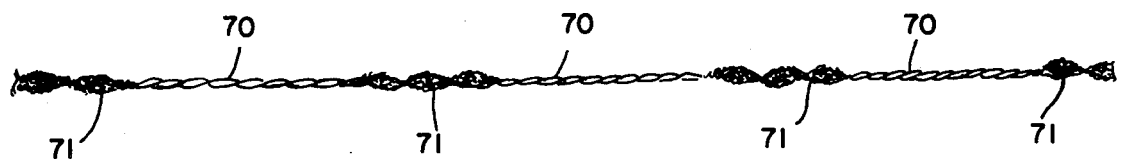
FIG. 7 is a schematic representation of a dental floss produced by the process and apparatus in FIG. 5.

FIG. 7 represents a dental floss of this invention. This floss has compacted zone or sections 70 separated by fluffed or beaded sections 71.

What is claimed is:

1. An apparatus for producing a novelty yarn having pronounced variations in linear density which comprises a fluid tangling means, means for introducing at least one multifilament yarn into said tangling means at a first predetermined rate, a reciprocating means for alternatingly positively and abruptly tensioning and relaxing the yarn being introduced into said tangling means by intermittently and abruptly changing the path of the yarn whereby said yarn is stretched during tensioning and abruptly made slack during relaxing to form sequential alternative segments of compact and fluffed filaments, and means for withdrawing the yarn from said tangling means at a second predetermined rate.

2. The apparatus of claim 1, wherein said reciprocating means comprises a rotating cam element, a cam follower biased against the cam element and mounted on a pivotal member, a yarn contacting arm operatively associated with said follower and yarn guide means for directing a multi-filament effect yarn introduced into said fluid tangling means along a prescribed path, said yarn contacting arm being actuated by said cam element to move from a normal position and to divert the effect yarn from its prescribed path to another path thereby creating tension on the effect yarn and subsequently to return to the normal position thereby causing the yarn to become slack and means for introducing a multi-filament core yarn into said tangling means in a relaxed state to combine with said effect yarn.

3. The apparatus of claim 1, wherein said fluid tangling means includes an air tangling jet and wherein the reciprocating means comprises a system of compound pulleys operatively associated with the air tangling jet, said system comprising a take-off pulley for a beaded yarn, a core pulley and an effect-producing pulley mounted on a single rotatable shaft and a guide means for guiding a core yarn to the core pulley into the air tangling jet from which the core yarn exits as a part of the beaded yarn to a take-off pulley that drives the shaft upon which said pulleys are mounted and then to a take-up package device and means for guiding the effect yarn around the effect pulley to a guide means for directing the effect yarn into the air tangling jet where the effect yarn combines with the core yarn and then exits as part of the beaded yarn.

4. An apparatus for making a novelty yarn including a core yarn and an effect yarn which comprises a fluid tangling means, first feed means for introducing the core yarn at a first predetermined rate into the fluid tangling means, second feed means for simultaneously introducing an effect yarn at a second predetermined rate into the fluid tangling means, said second predetermined rate being at least equal to the first predetermined rate, means for alternatively positively and abruptly tensioning and relaxing the effect yarn entering into the fluid tangling means by intermittently and abruptly changing the path of the yarn whereby said yarn is stretched during tensioning and abruptly made slack during relaxing and means for withdrawing the effect strand with the core strand at a third predetermined rate that is less than the first or the second predetermined rate to form a composite yarn wherein the effect yarn is alternately compacted and fluffed relative to the core yarn.

5. The apparatus of claim 4, further comprising means for combining a support yarn with the composite yarn and means for winding the combined yarn into a package.

6. An apparatus for making a novelty yarn including a core yarn and an effect yarn which comprises a fluid tangling means, first feed means for introducing the core yarn at a predetermined rate into the fluid tangling means, second feed means for simultaneously introducing an effect yarn at a predetermined rate into the fluid tangling means, means for alternatively positively tensioning and relaxing the effect yarn entering into the fluid tangling means, means for withdrawing the effect yarn with the core yarn at a predetermined rate that is less than the predetermined feed rates of the effect yarn and core yarn to form a composite yarn wherein the effect yarn is alternatively compacted and fluffed relative to the core yarn, means for combining a support yarn with the composite yarn, means for applying wax to the support yarn prior to combining the support yarn with the composite yarn and means for winding the combined yarn into a package.

7. The apparatus of claim 6, further comprising means for heating the yarn package for a short time to effect migration of the portion of the wax from the support yarn to the composite yarn.

8. An apparatus for making a dental floss which comprises a fluid tangling means, for tangling filaments of yarn introduced thereto, means for feeding a core strand of multi-filament yarn to said fluid tangling means at a predetermined first rate, second means for withdrawing the core strand at a predetermined second rate, third means for feeding at least one effect strand of multi-filament yarn at a predetermined third rate to the fluid tangling means and means for alternately tensioning and relaxing the effect strand of multi-filament yarn within the fluid tangling means and fourth means for withdrawing the effect strand with the core strand as a composite yarn, and means for combining the composite yarn resulting therefrom with a waxed support yarn and winding means for forming the combined yarn into a package, heater means for heating the package to migrate a portion of the wax from the support yarn to the combined yarn, and means for cooling the package to ambient conditions.

9. An apparatus for making a dental floss of claim 8, further comprising means for twisting the wax support yarn and the composite yarn together.

* * * * *